(12) United States Patent
Knight et al.

(10) Patent No.: US 8,778,637 B2
(45) Date of Patent: Jul. 15, 2014

(54) METHOD AND APPARATUS FOR APPLYING CONTINUOUS FLOW AND UNIFORM TEMPERATURE TO GENERATE THERMAL MELTING CURVES IN A MICROFLUIDIC DEVICE

(75) Inventors: Ivor T. Knight, Arlington, VA (US); Deborah J. Boyles, Sterling, VA (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 0 days.

(21) Appl. No.: 11/381,896

(22) Filed: May 5, 2006

(65) Prior Publication Data
US 2007/0231799 A1    Oct. 4, 2007

Related U.S. Application Data

(60) Provisional application No. 60/786,562, filed on Mar. 28, 2006.

(51) Int. Cl.
*C12P 19/34* (2006.01)

(52) U.S. Cl.
USPC ..................................................... 435/91.2

(58) Field of Classification Search
USPC ................................................. 435/6, 91.2
See application file for complete search history.

(56) References Cited

U.S. PATENT DOCUMENTS

| | | |
|---|---|---|
| 5,871,908 A | 2/1999 | Henco et al. |
| 6,140,054 A | 10/2000 | Wittwer et al. |
| 6,174,670 B1 | 1/2001 | Wittwer et al. |
| 6,403,338 B1 * | 6/2002 | Knapp et al. ............... 435/91.2 |
| 6,472,156 B1 | 10/2002 | Wittwer et al. |
| 6,569,627 B2 | 5/2003 | Wittwer et al. |
| 7,440,684 B2 * | 10/2008 | Spaid et al. ................ 392/466 |
| 2001/0036637 A1 | 11/2001 | Fujita et al. |
| 2001/0041357 A1 | 11/2001 | Fouillet et al. |
| 2002/0119442 A1 | 8/2002 | Dunlop et al. |
| 2003/0224434 A1 | 12/2003 | Wittwer et al. |
| 2004/0185452 A1 | 9/2004 | Chen et al. |
| 2005/0053950 A1 | 3/2005 | Zudaire Ubani et al. |
| 2005/0064465 A1 | 3/2005 | Dettloff et al. |
| 2005/0202470 A1 * | 9/2005 | Sundberg et al. ................ 435/6 |
| 2005/0282224 A1 | 12/2005 | Fouillet et al. |
| 2007/0026421 A1 * | 2/2007 | Sundberg et al. ................ 435/6 |

OTHER PUBLICATIONS

Obeid et al. Analytica Chimica Acta, vol. 494, pp. 1-9, 2003.*
Liao et al. Nucleic acids Research, vol. 33, No. 18, e156, pp. 1-7, Oct. 12, 2005.*

* cited by examiner

*Primary Examiner* — Cynthia B Wilder
(74) *Attorney, Agent, or Firm* — Rothwell, Figg, Ernst & Manbeck, P.C.

(57) ABSTRACT

The present invention provides a method for performing thermal melt analysis using a microfluidic device, the method comprising providing a microfluidic device having at least one microfluidic channel, introducing fluid comprising into the at least one microfluidic channel, continuously flowing the fluid through the at least one microfluidic channel while varying the temperature of the entire fluid stream as it moves through the at least one microfluidic channel by uniformly heating the entire fluid stream, and measuring, while continuously flowing the fluid through the at least one microfluidic channel, a detectable property emanating from the fluid.

24 Claims, 6 Drawing Sheets

METHOD AND APPARATUS FOR APPLYING CONTINUOUS FLOW AND UNIFORM TEMPERATURE TO GENERATE THERMAL MELTING CURVES IN A MICROFLUIDIC DEVICE

CROSS-REFERENCE TO RELATED APPLICATION

This application claims the benefit of U.S. Provisional Application No. 60/786,565, filed Mar. 28, 2006, which is hereby incorporated by reference in its entirety.

FIELD OF INVENTION

The present invention relates to the characterization of biological materials on a microfluidic device. More particularly, the present invention is directed towards determining the thermal properties of biological materials on a microfluidic device.

BACKGROUND OF THE INVENTION

When carrying out chemical or biochemical analyses, assays, syntheses or preparations, a large number of separate manipulations are performed on the material or component to be assayed, including measuring, aliquotting, transferring, diluting, mixing, separating, detecting, incubating, etc. Microfluidic technology miniaturizes these manipulations and integrates them so that they can be executed within one or a few microfluidic devices.

For example, pioneering microfluidic methods of performing biological assays in microfluidic systems have been developed, such as those described by Parce et al. in U.S. Pat. No. 5,942,443 entitled "High Throughput Screening Assay Systems in Microscale Fluidic Devices", and Knapp et al. in PCT Publication No. WO 98/45481 entitled "Closed Loop Biochemical Analyzers". Additionally, microfluidic devices for performing temperature-mediated reactions have been explored by Stern in U.S. Pat. No. 6,670,153.

One type of biological assay of particular interest in many fields of science is the detection and quantification of binding between various molecules. For example, screening of numerous compounds or molecules to determine how they bind to one another or how they bind to a particular target molecule is extremely important in many areas of research. For example, screening of large libraries of molecules is often utilized in pharmaceutical research. "Combinatorial" libraries composed of a collection of generated compounds, can be screened against a particular receptor to test for the presence of possible ligands and to quantify the binding of any possible ligands.

Various methods exist to characterize the binding between molecules. Many of those methods involve calorimetric analysis. Isothermal calorimetry (ITC) and differential scanning calorimetry (DSC) are examples of such methods. By measuring the thermal parameters of a binding reaction calorimeter can be used to test for the presence of binding between the molecules by detecting a shift in the thermal denaturation of a molecule that occurs when another molecule is bound to it. The shift in the thermal denaturation of a molecule (which could be as expressed in a molecular melt curve) can be monitored via the fluorescence of an indicator dye that binds to only select conformational states of the molecule. Alternatively, in some cases the binding between molecules can be determined by changes ill the intrinsic fluorescence of one of the molecules.

Characterization of the binding between molecules is also important tool in the characterization of nucleic acids. For example, Knapp et al. in U.S. Published Application No. 2002/0197630 entitled "Systems for High Throughput Genetic Analysis" discuss the use of melting curve analysis to detect single nucleotide polymorphisms (SNPs). Molecular melt curves (and differences between molecular melt curves) can also be used to detect and analyze sequence differences between nucleic acids. The thermal denaturation curve for nucleic acids can be monitored by, e.g., measuring thermal parameters, fluorescence of indicator dyes/molecules, fluorescence polarization, dielectric properties, or the like.

Melting curve analysis is typically carried out either in a stopped flow format or in a continuous flow format. In a stopped flow format, flow is stopped within a microchannel of a microfluidic device while the temperature in that channel is ramped through a range of temperatures required to generate the desired melt curve. A drawback to stopped flow format is that is does not integrated well in systems with other flow through processes which require the flow to continue without any stoppage. When fluorescent indicator dyes are used to monitor denaturation, another drawback to stopped flow format is the loss of fluorescent signal due to dye photobleaching while the thermal ramp is being performed.

In a continuous flow format, a melting curve analysis is performed by applying a temperature gradient along the length (direction of flow) of a microchannel of a microfluidic device. If the melting curve analysis requires that the molecules being analyzed be subjected to a range of temperatures extending from a first temperature to a second temperature, the temperature at one end of the microchannel is controlled to the first temperature, and the temperature at the other end of the length is controlled to the second temperature, thus creating a continuous temperature gradient spanning the temperature range between the first and second selected temperatures. A drawback to current implementations of continuous flow microchannel controlled to the first temperature, and the temperature at the other end of the length is controlled to the second temperature thus creating a continuous temperature gradient spanning the temperature range between the first and second selected temperatures. A drawback to current implementations of continuous flow format is that thermal properties of the molecules in the stream must be measured at multiple points along the temperature gradient to generate the desired melting curve. This is makes measurement of thermal properties of the molecules in the stream more complex than in the stopped flow format, where thermal properties of the molecules in the stream can be measured at a single point to generate the desired melting curve.

A welcome addition to the art would be a process that allows performance of thermal melting analysis for continuously flowing a fluid, material, etc. through at microchannel of a microfluidic device while varying the temperature of the entire fluid, material, etc. stream as it moves through the microchannel by uniformly heating the entire fluid, material, etc, stream. Such an addition to the art would enable the advantage of the continuous flow format, namely integration with continuous flow processes upstream and downstream of the thermal melt analysis, and permit measurement of thermal properties of molecules in the stream at a single point in the stream to (generate the desired melting curve. Furthermore, the problem of photobleaching will be greatly reduced because fluorescent dye molecules, continuously flowing past a point of measurement will be exposed to photobleaching radiation for much shorter periods than in the case of stopped flow analysis.

SUMMARY OF THE INVENTION

The present invention provides a method for performing thermal melt analysis in microfluidic devices. Molecule(s) to be assayed can be flowed through microchannels in the devices where the molecule(s) optionally are exposed to additional molecules constituting, e.g., fluorescence indicator molecules and/or binding partners of the molecule being assayed. The molecules involved are then heated (and/or cooled) and a detectable property of the molecules is measured over a range of temperatures. From the resulting data, a thermal property curve(s) is constructed which allows determination and quantification of the binding affinity of the molecules involved.

In one aspect, the present invention provides a method for performing thermal melt analysis of a nucleic acids in a microfluidic device, comprising of a microfluidic device having at least one microfluidic channel, introducing fluid comprising the nucleic acid and reagents into the at least one microfluidic channel, continuously flowing the fluid through the at least one microfluidic channel while varying the temperature of the entire fluid stream as it moves through the at least one microfluidic channel by uniformly heating the entire fluid stream, and measuring, while continuously flowing the fluid through the at least one microfluidic channel, a detectable property emanating from the fluid, wherein the detectable property indicates an extent of denaturation of the nucleic acid.

In the methods in accordance with the invention, heating comprises elevating the temperature of a molecule or molecules for a selected period of time. This period of time can range, e.g., from about 0.01 second through to about 1.0 minute or more, from about 0.1 second to about 10 seconds or more, or from about 0.01 second to about 1.0 second or more, including all time periods in between.

In other methods in accordance with the invention, heating comprises elevating the temperature of the molecule or molecules by continuously increasing the temperature of the molecule or molecules. For example, the temperature of the molecule(s) can be continuously increased at a rate in the range of $0.1°$ C./second to $1°$ C./second. Alternatively, the temperature of the molecule(s) can be continuously increase at a slower rate, such as a rate in the range of $0.01°$ C./second to $0.1°$ C./second, or at a faster rate, such as a rate in the range of $1°$ C./second to $10°$ C./second.

Heating the molecules optionally comprises elevating the temperature of the molecule(s) in the microchannel by either joule heating, non-joule heating, or both joule heating and non-joule heating. In one embodiment, joule heating is performed by flowing a selectable electric current through the microchannel, thereby elevating the temperature. Joule heating can occur over the entire length of the microchannel or within a given region of the microchannel. The level of joule heating can be controlled by changing the selectable current, the electrical resistance, or both the current and the resistance. The selectable current used for joule heating can include direct current, alternating current or a combination of direct current and alternating current. See, e.g., U.S. Pat. No. 5,965,410.

Optionally the heating used in the methods of the invention includes non-joule heating, e.g., through application of an internal or an eternal heat source. In one embodiment, the internal or external heat source includes a thermal heating block, just as for joule heating, non-joule heating can occur over the entire length of the microchannel or within region of the microchannel Heating methods in accordance with the invention also encompass uniformly applying a temperature along the entire length of a microchannel or within a given region of the microchannel. Once a steady state flow of fluid through the portion of the microchannel is established, a uniform temperature will be established within that fluid. When Joule heating is used, a uniform temperature can be established along the entire length of a microchannel or within a given region of the microchannel by fabricating the channel so that it maintains a constant cross-sectional area along its length, and then applying a single electric current through that length. One method of establishing a uniform temperature along the length of a microchannel when non-joule heating is employed is to place a thermal block in contact with the microchannel, and to establish a uniform temperature across the block in the direction corresponding to the length direction of the microchannel using heating or cooling elements.

In another aspect of the invention, the methods of detecting a property of the molecule(s) involved comprises detecting a level of fluorescence or emitted light from the molecules(s) that varies as a function of relative amounts of binding. In one configuration, the detecting of fluorescence involves a first molecule and a second molecule, wherein the first molecule is a fluorescence indicator dye or a fluorescence indicator molecule and the second molecule is the target molecule to be assayed. In one embodiment, the fluorescence indicator dye or fluorescence indicator molecule binds or associates with the second molecule by binding to hydrophobic or hydrophilic residues on the second molecule. The methods of detecting optionally further comprise exciting the fluorescence indicator dye or fluorescence indicator molecule to create an excited fluorescence indicator dye or excited fluorescence indicator molecule and discerning and measuring an emission or quenching event of the excited fluorescence indicator dye or fluorescence indicator molecule.

Another aspect of the methods of the invention includes generating a thermal property curve. One embodiment of generating a thermal property curve includes providing one molecule comprising a fluorescence indicator dye or fluorescence indicator molecule, and at least a second molecule comprising, one or more of: an enzyme, a ligand, a peptide nucleic acid, a cofactor, a receptor, a substrate, a protein, a polypeptide, a nucleic acid (either double-stranded or single-stranded), an antibody, an antigen, or an enzyme complex. A fluorescence of the first molecule in the presence of the second molecule as a function of temperature is measured and the resulting data is used to generate a thermal property curve.

An additional embodiment of generating the thermal property curve comprises measuring a change in the fluorescence of one molecule that is correlative or proportional to a change in a physical property of another molecule(s) due to a change in temperature. A further embodiment includes generating a thermal property curve control curve by measuring fluorescence of a first molecule in the presence of a second molecule as a function of temperature, where the first molecule is a fluorescence indicator dye or molecule and the second molecule is: a protein, a polypeptide an enzyme, an enzyme complex, a nucleic acid (either single-stranded or double-stranded), a ligand, a peptide nucleic acid, a cofactor, a receptor, an antibody, an antigen, or a substrate.

In yet another embodiment, methods in accordance with the invention include generating a thermal property curve where a first molecule and at least a second molecule are proteins, polypeptides, enzymes, enzyme complexes, nucleic acids (both double-stranded anti single-stranded), ligands, peptide nucleic acids, cofactors, receptors, antibodies, antigens, or substrates. In these embodiments, generating a thermal property curve comprises measuring a change in the thermal parameters of the system comprising the molecule(s) in the microchannel as a function of temperature when a first molecule is in the presence of at least a second molecule. An additional embodiment entails generating a control curve by measuring the change in the total free energy of the system as a function of temperature without the presence of a second molecule.

In another aspect, the invention includes microfluidic systems comprising a microfluidic device having body structure containing at least one fluidic microchannel; a fluid direction system for controllably moving reagents into and through the microchannel; at least one energy source for controllably heating the reagents in the microchannel; a source of a fluorescence indicator dye or fluorescence indicator molecule fluidly coupled to the microchannel; a source of one or more sample molecules to be assayed fluidly coupled to the microchannel; an excitation source for the fluorescence indicator dye or fluorescence indicator molecule; a detector proximal to the body structure for detecting a change in a physical property of the one or more sample molecules; and, a computer operably coupled to the detector, containing an instruction set for acquiring data from the detector and for constructing thermal melt curves and control curves from the data.

In another embodiment, the integrated system or microfluidic devices of the invention include a fluid direction system which, during operation, controllably determines the selection of one or more reagent(s) to be added to the microchannel; the amount of one or more reagent(s) to be added to the microchannel; the time at which one or more reagent(s) is to be added to the microchannel; and the speed at which one or more reagent(s) is to be added to the microchannel.

In another embodiment, the integrated system or microfluidic devices of the invention include at least one energy source which, during operation, elevates the temperature of the molecule(s) in the microchannel by either joule heating, non-joule heating or both joule heating and non-joule heating.

Joule heating in the integrated system or microfluidic device of the invention comprises the flow of a selectable electric current through the at least one microchannel, thereby elevating the temperature. Joule heating can be applied uniformly over the entire length of the microchannel, maintaining a consistent cross-sectional area of the channel. The level of joule heating is controlled by changing the selectable current, the electrical resistance of the fluid in the channel, or both the current and the resistance. The selectable current may comprise a direct current, an alternating current or a combination of direct current and alternating current.

Optionally, the integrated system or microfluidic device of the invention includes non-joule heating through an internal or external heat source. In some embodiments, the internal or external heat source may comprise one or more of a thermal heating block. Peltier device, resistive heating element, thermoelectric gas or liquid that transfers heat conductively or convectively. Just as for joule heating, non-joule heating optionally can produce a uniform temperature over the entire length of the microchannel.

In another embodiment of the invention, the integrated system or microfluidic device optionally provides at least one fluorescence indicator dye or fluorescence indicator molecule capable of binding to one or more hydrophobic amino acid residues, one ore more hydrophillic amino acid residues, or a combination thereof, of another molecule. For example, the fluorescence indicator dye or fluorescence indicator molecule comprises, e.g., 1-analino-naphthalene-8-sulfonate. In another embodiment, the fluorescence indicator dye or fluorescence indicator molecule can intercalate into, or bind by another mechanism to, one or more nucleic acid polymers.

In various embodiments, an integrated system or microfluidic device in accordance with the invention may comprise a high-through-put format, a low-throughput throughput format, or a multiplex format. In many embodiments of the invention the excitation source for exciting the fluorescence indicator dye or fluorescence indicator molecule comprises a light source. For example, the light source may comprise one of more of a tungsten-halogen lamp, a xenon-arc lamp, a mercury lamp, a laser, an LED, or a fiber optic cable. Some embodiments of the integrated system comprise an array of light sources to excite fluorescence at a plurality of locations along the length of a microchannel in the microfluidic device.

An integrated system in accordance with the invention may comprise one or more of the following types of optical detectors: a fiber optic probe, a charge coupled device, a fluorescence imaging camera, a photomultiplier, a photodiode, or a more of the following types of optical detectors: a fiber optic probe, a charge coupled device, a fluorescence imaging camera, a photomultiplier, a photodiode, or a fluorescence polarization sensor. The system may also comprise an array of optical detectors to measure optical signals emanating from a plurality of locations along the length of a microchannel in the microfluidic device. Additionally, an integrated system in accordance with the invention may comprise one or more of the following types of temperature detectors: contact temperature detectors such as thermocouples, resistance temperature detectors, or thermistors; or non-contact temperature detectors such as IR thermometers or optical pyrometers. The system may also comprise an array of temperature detectors to measure the temperature at a plurality of locations along the length of a microchannel in the microfluidic device. The optical detector optionally has the ability to detect fluorescence or emitted from an excited fluorescence indicator dye or molecule or optionally has the ability to detect a change in the thermal parameters of the system comprising the molecule(s) in the at least one microchannel.

DETAILED DESCRIPTION OF THE INVENTION

Figure 1:
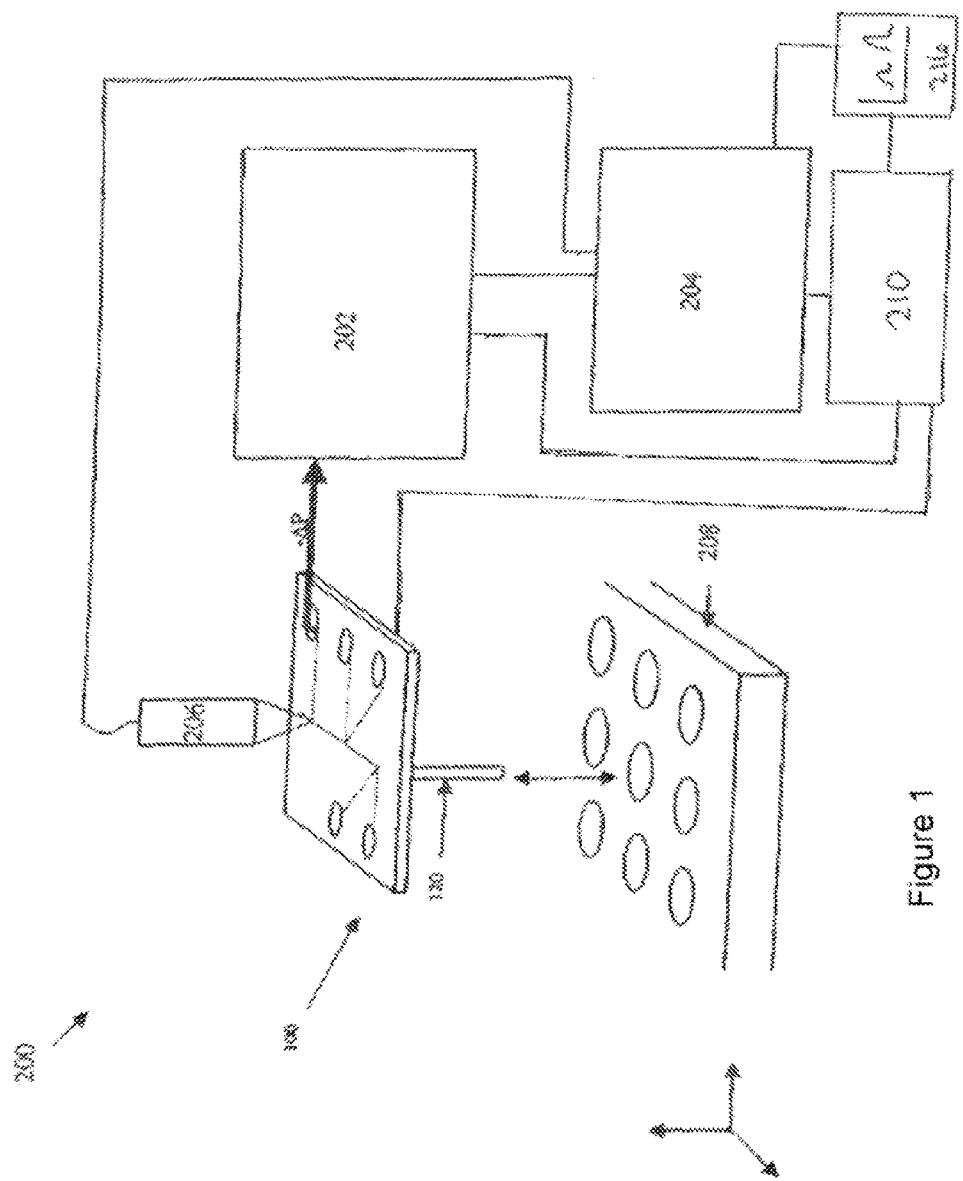
FIG. 1 is a schematic of a system comprising a computer, detector and temperature controller.

Methods and devices in accordance with the invention are capable of rapidly characterizing a variety of biological materials via the generation of molecular melt curves. For example, the molecular melt curve of a double stranded DNA molecule can provide information about the number of base pairs in the molecule, the GC content, and the amount of variation from ideal Watson-Crick base pairing. A molecular melt curve also can be used to indicate the degree of binding between one or more test molecules and a target molecule. "Binding" includes not only, e.g., receptor-ligand interactions, but also, e.g., nucleic acid-nucleic acid hybridization interactions and can include both specific and nonspecific interaction. If the test molecules do bind to the target molecule, then their binding can be quantified by the invention. The methods and devices herein are flexible and can be applied to many different types of compounds and molecules. For example, both the target molecule and the test molecules can be any one or more of, e.g., a protein (whether enzymatic or not), an enzyme, a nucleic acid (e.g., DNA and/or RNA, including, single-stranded, double-stranded, or triple-stranded molecules), a ligand, a peptide nucleic acid, a cofactor, a receptor, a substrate, an antigen, a polypeptide, monomeric and multimeric proteins (either homomeric or heteromeric), synthetic oligonucleotides, portions of recombinant DNA molecules or chromosomal DNA, portions or pieces of proteins/peptides/receptors/etc. that are capable or having secondary, tertiary, or quandary structure, etc. The target molecule also optionally interacts with, e.g., co-enzymes, co-factors, lipids, phosphate groups, oligosaccharides, or prosthetic groups.

Briefly, the methods and devices of the invention enable the construction of and comparison of molecular melt curves. Molecular melt curves are alternatively described as "thermal melting curves", "thermal melt curves", "thermal property curves", "thermal denaturation curves" or "thermal profile curves." Accordingly, an analysis involving the generation of molecular melt curve can also be described as a molecular melt analysis, a thermal melting analysis, a thermal melt analysis, a thermal property analysis, a thermal denaturation analysis, or a thermal profile analysis. In such an analysis, a sample of a target molecule, or target molecules, to be tested is flowed into one or a number of microchannels in a microfluidic device. Optionally, the target molecule is then contacted with one or more test molecules that are screened for possible binding capability with the target molecule and/or with an indicator such as a fluorescence indicator dye or molecule. Optional embodiments of the present invention allow for multiple configurations of, e.g., heat application, flow speed, reagent composition, binding conditions, and timing of all the multiple variants involved.

Once the test molecule interacts with the target molecule and/or labeling compound, the present invention sets the reaction conditions, in a controllable manner, to a desired temperature (either continuously over a range of temperatures or non-continuously to discrete temperature points). Selected physical properties of the molecules are measured in the microfluidic device and thermal property curves produced from the measurements. The thermal property curves are based upon, e.g., the temperature induced denaturation or unfolding that occurs when the molecules are subjected to heat. Denaturation can include, e.g., loss of secondary, tertiary, or quaternary structure by means of uncoiling, untwisting, or unfolding, disassociation of nucleic acid strands, etc.

Numerous types of molecules can be assayed by the methods, devices, and systems of the present invention. For example, screening for interactions between hydridization probes and nucleic acids, e.g., comprising single nucleotide polymorphisms (SNPs), can be accomplished through use of the current invention. For examples of types of molecular interactions optionally assayed by the invention, see, e.g., Pilch, D. et al., (1994) "Ligand-induced formation of nucleic acid triple helices." *Proc Natl Acad Sci USA*, 91(20):9332-9336; Barcelo, F. et al. (1990) "A scanning calorimetric study of natural DNA and antitumoral anthracycline antibiotic-DNA complexes." *Chem Biol Interact*, 74(3):315-324; Gundry, C. et al. (2003) "Amplicon melting analysis with labeled primers: A closed-tube method for differentiating homozygotes and heterozygotes." *Clin Chem* 49(3):396-406; and Zhou, L. et al. (2004) "Closed tube genotyping with unlabeled oligonucleotide probes and a saturating DNA dye." *Clin Chem* 50(8):1328-1335.

The actual detection of a change(s) in a physical property of the molecules can be detected in numerous methods depending on the specific molecules and reactions involved. For example, the denaturation of the molecules can the tracked by following fluorescence or emitted light from molecules in the assay. The degree of, or change in, fluorescence is correlational or proportional to the degree of change in conformation of the molecules being assayed. The methods and devices of the invention allow for various methods of exciting the molecules involved in the assay, through use of, e.g., lasers, lights, etc. The fluorescence can be intrinsic to the molecules being assayed, e.g., from tryptophan residues in the molecules, or extrinsic to the molecules being assayed, e.g., from fluorophores added to the assay mixture in the microfluidic device. The change(s) in fluorescence or emitted light can optionally be detected in a number of ways according to the specific needs of the assay desired. For example, a charge-coupled device is utilized as an optional part of the device.

The change in fluorescence of emitted light indicates a change in conformation of the target molecule and from which the thermal property curve is constructed. Displacement or shift of the thermal property curve when the target molecule is in the presence of a test molecule allows detection and quantification of binding between the test molecule and the target molecule(s).

System Example

FIG. 1 depicts a system known in the art in which the present invention can be implemented. Briefly, system 200 includes microfluidic device 100, detector 206, computer 204, fluid direction system 202, microwell plate 208, temperature control system 210 and monitor 216.

Detector 2406 detects signals from, among other items, materials flowing through the microfluidic channel(s) of microfluidic device 100. Computer 204 digitizes, stores, and manipulates signal information detected by detector 206. Monitor 216 displays the data produced by microfluidic device 100. Microwell plate 208 includes sample materials in the wells of the plate. Fluid direction system 202 controls the flow of the fluid through the microfluidic channels of microfluidic device 100. Temperature control system 210 controls heating of the microfluidic channel of microfluidic device 100. Please note that the invention is not limited to being implemented in the above described system, and can be implemented in any system in which a microfluidic device is used to determine the thermal characteristics of biological material.

Thermal Property Curves

The unfolding, disassociation or denaturing of a target molecule(s) in response to changes in temperature can be useful in many applications e.g., in the identification of a nucleic acid, the detection of SNPs in a nucleic acid, etc. The measurement of the molecular denaturing, disassociation or unfolding of the target molecule is used to construct a thermal property curve. In other applications, variations of basic thermal property, curves can be used to test for, e.g., hybridization of specific oligonucleotides to each other. See, e.g., Zhou, L. et al. (2004) "Closed tube genotyping with unlabeled oligonucleotide probes and a saturating DNA dye." *Clin Chem* 50(8):1328-1335 . . . .

Fluorescence—

In one embodiment of the present invention, spectroscopy is used to measure changes in fluorescence or light to track the denaturation/unfolding of the target molecule as the target molecule is subjected to changes in temperature. Spectrometry, e.g., via fluorescence is a useful method of detecting thermally induced denaturation/unfolding of molecules. Many different methods involving fluorescence are available for detecting denaturation of molecules (e.g., intrinsic fluorescence, numerous fluorescence indicator dyes or molecules, fluorescence polarization, fluorescence resonance energy transfer, etc.) and are optional embodiments of the present invention. These methods can take advantage of either internal fluorescent properties of target molecules or external fluorescence, i.e. the fluorescence of additional indicator molecules involved in the analysis.

Fluorescence Indicator Dyes and Molecules—

A method of measuring the degree of denaturation/unfolding of the target molecule is through monitoring of the fluorescence of indicator dyes or molecules added to the microfluidic device along with the target molecule and any test molecules of interest. "Fluorescence indicator dye" or "fluorescence indicator molecule" refers to a fluorescent molecule or compound (i.e., a fluorophore) which can bind to a target molecule either once the target molecule is unfolded or denatured or before the target molecule undergoes conformational change by, e.g., denaturing and which emits fluorescent energy or light after it is excited by, e.g., light of a specified wavelength. "Fluorescence indicator dye" and "fluorescence indicator molecule" includes all fluorophores.

For example, fluorescence dyes which bind specifically to certain regions on molecules are optionally used in the present microfluidic device to monitor the molecular unfolding/denaturation of the target molecule due to temperature. One example of a group of such fluorescence dyes consists of dyes that bind specifically to hydrophobic areas of molecules. An illustrative, but not limiting, example of a dye in that group is 1-anilino-8-naphthlalene sulfonate (ANS). ANS has a low fluorescence in polar environments, but when it binds to apolar regions, e.g., such as those found in interior regions of natively folded proteins, its fluorescence yield is greatly enhanced. As target molecules are denatured, e.g., as happens with increasing temperature in the microfluidic device, they become denatured thereby allowing solvent, e.g., water, to reach and quench the fluorescence of the ANS. Alternatively, ANS can be used to monitor temperature induced conformational changes in other ways as well depending on the specific molecules/reaction/etc. being studied in the microfluidic device of the invention (e.g., the path of denaturation of a protein can create hydrophobic regions to which ANS can bind and fluoresce; alternatively, denaturation allows creation of hydrophobic protein globules to which ANS can bind; ANS fluorescence can be monitored as ANS competes with ligands for binding sites on proteins, etc.). See, e.g., Schonbrunn, E. et al. (2000) "Structural basis for the interaction of the fluorescence probe 8-anilino-1-naphthalene sulfonate (ANS) with the antibiotic target MurA" *Proc Natl Acad Sci USA* 97(12):6345-6349; and Ory, J. et al., (1999) "Studies of the Ligand Binding Reaction of Adipocyte Lipid Binding Protein Using the Fluorescent Probe 1,8-Anilinonaphthalene-8-Sulfonate" *Biophys* 77:1107-1116. Various other hydrophobic fluorescence dyes, etc. are well known to those in the art as are fluorescence dyes which bind to other specific classes of areas on target molecules to be assayed in the microfluidic device and which are optionally embodied in the current invention.

Another optional dye type used in the current microfluidic device is one that intercalates within strands of nucleic acids. The classic example of such type of dye is ethidium bromide. An example of use of ethidium bromide for binding assays includes, e.g., monitoring for a decrease in fluorescence emission from ethidium bromide due to binding of test molecules to nucleic acid target molecules (ethidium bromide displacement assay). See, e.g., Lee, M. et al., (1993) "In vitro cytotoxicity of GC sequence directed alkylating agents related to distamycin" *J Med Chem* 36(7):863-870. The use of nucleic acid intercalating agents in measurement of denaturation is well known to those in the art. See, e.g., Haugland (1996) Handbook of Fluorescent Probes and Research Chemicals Published by Molecular Probes, Inc., Eugene, Oreg.

Dyes that bind to nucleic acids by mechanisms other than intercalation can also be employed in embodiments of the invention. For example, dyes that bind the minor groove of double stranded DNA can be used to monitor the molecular unfolding/denaturation of the target molecule due to temperature. Examples of suitable minor groove binding dyes are the SYBR Green family of dyes sold by Molecular Probes Inc. of Eugene Oreg. See, e.g., Haugland (1996) Handbook of Fluorescent Probes and Research Chemicals Published by Molecular Probes, Inc., Eugene, Oreg., SYBR Green dyes will bind to any double stranded DNA molecule. Within a SYBR Green dye binds to double stranded DNA, the intensity of the fluorescent emissions increases. As more double stranded DNA are denatured due to increasing temperature, the SYBR Green dye signal will decrease.

Fluorescence Polarization—

Other embodiments of the invention utilize fluorescence polarization. Fluorescence polarization (FP) provides a useful method to detect hybridization formation between molecules of interest. This method is especially applicable to hybridization detection between nucleic acids, e.g., to monitor single nucleotide polymorphisms (SNPs).

Generally, FP operates by monitoring, the speed of rotation of fluorescent labels, such as fluorescent dyes, e.g., before, during, and/or after binding events between molecules that comprise the test and target molecules. In short, binding of a test molecule to the target molecule ordinarily results in a decrease in the speed of rotation of a bound label on one of the molecules, resulting in a change in FP.

For example, when a fluorescent molecule is excited with a polarized light source, the molecule will emit fluorescent light in a fixed plane, e.g., the emitted light is also polarized, provided that the molecule is fixed in space. However, because the molecule is typically rotating and tumbling in space, the plane in which the fluoresced light is emitted varies with the rotation of the molecule (also termed the rotational diffusion of the molecule). Restated, the emitted fluorescence is generally depolarized. The faster the molecule rotates in solution, the more depolarized it is. Conversely, the slower the molecule rotates in solution, the less depolarized, or the more polarized it is. The polarization value (P) for a given molecule is proportional to the molecule's "rotational correlation time," or the amount of time it takes the molecule to rotate through an angle of approximately 68.5°. The smaller the rotational correlation time, the faster the molecule rotates, and the less polarization will be observed. The larger the rotational correlation time, the slower the molecule rotates, and the more polarization will be observed. Rotational relaxation time is related to viscosity ($\eta$) absolute temperature (T), molar volume (V), and the gas constant (R). The rotational correlation time is generally calculated according to the following formula: Rotational Correlation Time=$3\eta V/RT$. As can be seen from the above equation, if temperature and viscosity, are maintained constants then the rotational relaxation time, and therefore, the polarization value, is directly related to the molecular volume. Accordingly, the larger the molecule, the higher its fluorescent polarization value, and conversely, the smaller the molecule, the smaller its fluorescent polarization value.

In the performance of fluorescent binding assays in the current invention, a typically small, fluorescently labeled molecule, e.g., a ligand, antigen, etc., having a relatively fast rotational correlation time, is used to bind to a much large molecule, e.g., a receptor protein, antibody, etc., which has a much slower rotational correlation time. The binding of the small labeled molecule to the larger molecule significantly increases the rotational correlation time (decreases the amount of rotation) of the labeled species, namely the labeled complex over that of the free unbound labeled molecule. This has a corresponding effect on the level of polarization that is detectable. Specifically, the labeled complex presents much higher fluorescence polarization than the unbound, labeled molecule.

In addition to Nikiforov and Jeong "Detection of Hybrid Formation between Peptide Nucleic Acids and DNA by Fluorescence Polarization in the Presence of Polylysine" (1999) *Analytical Biochemistry* 275:248-253, other references that discuss fluorescence polarization and/or its use in molecular biology include Perrin "Polarization de la lumiere de fluorescence. Vie moyeene de molecules dans l'etat excite" (1926) *J Phys Radium* 7:390; Weber (1953) "Rotational Brownian motion and polarization of the fluorescence of solutions"*Adv Protein Chem* 8:415; Weber (1956) *J Opt Soc Am* 46:962; Dandliker and Feigen (1961), "Quantification of the antigen-antibody reaction by the polarization of fluorescence" *Biochem Biophys Res Commun* 5:299; Dandliker and de Saussure (1970) (Review Article) "Fluorescence polarization in immunochemistry" *Immunochemistry* 7:799; Dandliker W. B., et al. (1973), "Fluorescence polarization immunoassay. Theory and experimental method"*Immunochemistry* 10:219; Levison S. A., et al. (1976), "Fluorescence polarization measurement of the hormone-binding site interaction" *Endocrinology* 99:1129; Jiskoot et all. (1991), "Preparation and application of a fluorescein-labeled peptide for determining the affinity constant of a monoclonal antibody-hapten complex by fluorescence polarization" *Anal Biochem* 196:421; Wei and Herron (1993), "Use of synthetic peptides as tracer antigens in fluorescence polarization immunoassays of high molecular weight analytes" *Anal Chem* 65:3372; Devlin et al. (1993), "Homogeneous detection of nucleic acids by transient-state polarized fluoresence" *Clin Chem* 39:1939; Murakami et al. (1991). "Fluorescent-labeled oligonucleotide probes detection of hybrid formation in solution by fluorescence polarization spectroscopy" *Nuc Acids Res* 19:4097. Checovich et al. (1995), "Fluorescence polarization—a new tool for cell and molecular biology" (product review), *Nature* 375:354-256 Kumke et al. (1995), "Hybridization of fluorescein-labeled DNA oligomers detected by fluorescence anisotropy with protein binding enhancement" *Anal Chem* 67(21):3945-3951; and Walker, J. et al. (1996), "Strand displacement amplification (SDA) and transient-state fluorescence polarization detection of mycobacterium tuberculosis DNA" *Clinical Chemistry* 42(1):9-13.

Fluorescence Resonance Energy Transfer—

Yet another optional embodiment of the invention uses fluorescence resonance energy transfer (FRET) to track the conformational changes of the target molecule (and interactions with test molecules which can bind with the target molecule) as a function of temperature. FRET relies on a distance-dependent transfer of energy from a donor fluorophore can be transferred to the fluorophore. If an acceptor fluorophore is in close proximity to an excited donor fluorophore then the emission of the donor fluorophore can be transferred to the acceptor fluorophore. This causes a concomitant reduction in the emission intensity of the donor fluorophore and an increase in the emission intensity of the acceptor fluorophore. Since the efficiency of the excitation transfer depends, inter alia, on the distance between the two fluorophores, the technique can be used to measure extremely small distances such as would occur when detecting changes in conformation. This technique is particularly suited for measurement of binding reactions, protein-protein interactions, e.g., such as a protein of interest binding to an antibody and other biological events altering the proximity of two labeled molecules. Many appropriate interactive labels are known. For example, fluorescent labels, dyes, enzymatic labels, and antibody labels are all appropriate. Examples of interactive fluorescent label pairs include terbium chelate and TRITC (tetrarhodamine isiothiocyanate), europium cryptate and Allophycocyanin, DABCYL and EDANS and many others known to those of skill (e.g., donor fluorophores such as carboxyfluorescein, iodacetamidofluorescein, and fluorescein isothiocyanate and acceptor fluorophores such as iodoacetamidoeosin and tetramethylrhodamine). Similarly, two colorimetric labels can result in combinations which yield a third color, e.g., a blue emission in proximity to a yellow emission provides an observed green emission. With regard to fluorescent pairs, there are a number of fluorophores which are known to quench one another. Fluorescence quenching is a bimolecular process that reduces the fluorescence quantum yield, typically without changing the fluorescence emission spectrum. Quenching can result from transient excited state interactions, (collisional quenching) or, e.g., from the formation of non-fluorescent ground state species. Self quenching is the quenching of one fluorophore by another; it tends to occur when high concentrations, labeling densities, or proximity of labels occurs. FRET is a distance dependent excited state interaction in which emission of one fluorophore is coupled to the excitation of another that is in proximity (close enough for an observable change in emissions to occur). Some excited fluorophores interact to form excimers, which are excited state dimers that exhibit altered emission spectra (e.g., phospholipid analogs with pyrene sn-2 acyl chains). See, e.g., Haugland (1996) Handbook of Fluorescent Probes and Research Chemicals Published by Molecular Probes, Inc., Eugene, Oreg., e.g., at chapter 13; and Selvin, P. (2000) "The renaissance of fluorescence energy transfer" *Nat Struct Biol* 7(9); 730-734.

Molecular Beacons—

Other optional embodiments of the invention use molecular beacons in following the conformation changes of target molecules/test molecules as a function of temperature. Molecular beacons are probes (i.e., test molecules in terms of the present invention) that can be used to report the presence of specific nucleic acids. They are especially useful in situations where it is either undesirable or not possible to isolate the nucleic acid hybrids being assayed.

Structurally, molecular beacons are hair-pin shaped nucleic acid molecules having a center 'loop' section of a specific nucleic acid sequence flanked by two complementary end regions (annealed together), one of which has a fluorescence moiety and the other a quencher moiety. The loop region is complementary to a target or specific nucleic acid sequence. When the molecular beacon is not in the presence of its proper target molecule and is in its hairpin conformation, the fluoresence moiety and quencher moiety are in close enough proximity that the fluoresence is quenched and the energy is emitted as heat. However, when the molecular beacon encounters its proper target molecule it changes conformation so that its internal loop region binds to the target nucleic acid sequence. This forces the fluorescence moiety to move away from the quencher moiety, which leads to a restoration of fluoresence. Through use of different fluorophores, molecular beacons can be made in a variety of different colors. DABCYL (a non-fluorescent chromophore) usually serves as the universal quencher in molecular beacons. Molecular beacons can be very specific and thus be used to detect e.g., single nucleotide differences between molecules in the present invention. See, e.g., Tyagi, S. et al. (1996) "Molecular beacons: probes that fluoresce upon hybridization" *Nat Biotech* 14:303-308; and Tyagi, S. et al. (1998) "Multicolor molecular beacons for allele discrimination" *Nat Biotech* 16:49-53.

Circular Dichroism—

Another optional embodiment of the invention uses circular dichroism (CD) to follow the conformational changes of the target molecules/text molecules as a function of temperature. CD is a type of light absorption spectroscopy which measures the difference in absorbance by a molecule between right-circularly polarized light and left-circularly polarized light. CD is quite sensitive to the structure of polypeptides and proteins. For reviews of the application and technique of CD, see, e.g., Woody, R. (1985) "Circular Dichroism of Peptides" in The Peptides 7:14-114, Academic Press; Johnson, W. (1990) "Protein Secondary Structure and Circular Dichroism: A Practical Guide" *Proteins* 7:205-214. In order to construct molecular melt curves, the present invention optionally uses CD to follow the conformational changes in the target and test molecules caused by changes in temperature.

UV Absorbance

Optional embodiments of the invention include the use of measurement of UV Absorbance to detect and/or track denaturation of nucleic acid molecules, and/or to quantify the total amount of nucleic acid. UV can be employed to measure the extent of denaturation because the UV absorbance value of single stranded nucleic acid molecules is greater than the absorbance value of double stranded nucleic acid molecules.

Integrated Systems, Methods and Microfluidic Devices of the Invention

In addition to the actual detection of conformational changes and construction of thermal property curves, the microfluidic devices of the invention also include numerous optional variant embodiments for e.g., fluid transport, temperature control, fluorescence detection and heating.

The term "microfluidic device" refers to a device having fluidic channels or chambers that are generally fabricated at the micron to sub-micron scale, e.g., the channel or chamber typically having at least one cross-sectional dimension in the range of less than about 1 mm. The channels in a microfluidic device are sometimes referred to as "microfluidic channels". Microfluidic channels are typically closed channels within the interior of a microfluidic device. In many microfluidic devices, the channels are formed by fabricating grooves on the surface of a first planar substrate, and then enclosing those groove by attaching a second planar substrate to that surface. An integrated system, or microfluidic system, interfaces with the microfluidic device. In many microfluidic systems the microfluidic device is a removable component like a cartridge. Microfluidic devices in accordance with current invention can be fabricated from materials that are compatible with the conditions present in the specific experiments, etc. under examination. Such conditions include, but are not limited to, pH, temperature, ionic concentration, pressure, and application of electrical fields. For example, as described throughout, the systems mentioned can utilize temperature control to provide thermal melting curves according to the methods herein. Accordingly, materials can be selected to provide particular properties at any selected temperature. The materials of the device are also chosen for their inertness to components of the experiments to be carried out in the device. Such materials include, but are not limited to, glass, quartz, silicon, and polymeric substrates, e.g., plastics, depending on the intended application.

Although the devices and systems specifically illustrated herein are generally described in terms of the performance of a few or one particular operation, it will be readily appreciated from this disclosure that the flexibility of these systems permits easy integration of additional operations into these devices. For example, the devices and systems described will optionally include structures, reagents and systems for performing virtually any number of operations. Such operations include sample handling and preparation operations, e.g., cell separation, extraction, purification, amplification, cellular activation, labeling reactions, dilution, aliquotting, and the like.

Integrated microfluidic systems in accordance with the present invention can include other features such as a fluid transport system that directs fluid and possibly particle movement within the microchannels. The fluid transport system could conceivably employ any fluid movement mechanism known in the art (e.g., fluid pressure sources for modulating fluid pressure in the microchannels, electrokinetic controllers for modulating voltage or current in the microchannels gravity flow modulators, magnetic control elements for modulating a magnetic field within the microchannels, or combinations thereof).

The microfluidic devices of the invention can also include fluid manipulation elements such as a parallel stream of reagents into parallel streams of reagents conversion of at least one serial stream of reagents into parallel streams of reagents for parallel delivery of reagents to a reaction site or reaction sites within the device. For example, the systems herein (optionally include a valve manifold and plurality of solenoid valves to control flow switching, between channels and/or to control pressure/vacuum levels in the microchannels, e.g., analysis or incubation channels. Another example of a fluid manipulation element includes, e.g., a capillary optionally used to sip a sample or samples from a microtiter plate and to deliver it to one of a plurality of channels e.g., parallel reaction or assay channels. Additionally, molecules, etc. are optionally loaded into one or more channels of a microfluidic device through one pipettor capillary fluidly coupled to each of one or more channels and to a sample or particle source, such as a microwell plate.

The system is described herein optionally, include microfluidic devices as described above, in conjunction with additional instrumentation for controlling fluid transport, flow rate and direction within the devices, detection instrumentation for detecting or sensing results of the operations performed by the system, processors, e.g., computers, for instructing the controlling instrumentation in accordance with preprogrammed instructions, receiving data from the detection instrumentation, and for analyzing, storing and interpreting the data, and providing the data and interpretations in a readily accessible reporting format.

Temperature Control

Embodiments of the present invention use temperature control to effectuate molecular melting or denaturation for the melting curve assays. Integrated systems in accordance with the invention can also control temperatures to control reaction parameters, e.g., in thermocycling reactions (e.g., PCR, LCR), or to control reagent properties. In general, and in embodiments of the invention, a variety of heating methods can be used to provide a controlled temperature in miniaturized fluidic systems. Such heating methods include both joule and non-joule heating. Non-joule heating methods can be internal to the microfluidic device, i.e., integrated into the structure of the microfluidic device, or external, i.e., separate from the microfluidic device, but part of the microfluidic system. Non-joule heating can be implemented by photon beams, conductive or convective heating and cooling via a fluid (e.g. passing a liquid through channels in the device, or contacting one or more external surfaces of the device with a gas or liquid), lasers, electromagnetic fields, electron beams, thermoelectric heaters, furnaces, resistive thin films, resistive heating coils, peltier heaters, and thermoelectric heaters or coolers. Many of those non-joule heating methods can be used in conjunction with a thermal block, which is a block of thermally conducting material in thermal contact with an external surface of the microfluidic device that transfers thermal energy to or from the microfluidic device by conduction. The block of the thermally conducting material is in "thermal contact" with the microfluidic channels within the interior of the microfluid device in that temperature changes in the block will cause temperature changes in the microfluidic channels. The temperature of the thermal block can be manipulated using one or more of the previously listed non-joule heating methods. For example, the temperature of the thermal block could be manipulated by controlling the current passing through resistive heaters in thermal contact with the thermal block, or by controlling the current passing through a peltier device. An controller in the system interfacing with the microfluidic device, or within the microfluidic device itself can be used to regulate the temperature involved. These examples are not limiting and numerous other energy sources can be utilized to raise the fluid temperature in the microfluidic device.

Non-joule heating units can attach directly to an external portion of a chip of the microfluidic device. Alternatively, non-joule heating units can be integrated into the structure of the microfluidic device. In either case, the non-joule heating is optionally applied to only selected portions of chips in microfluidic devices or optionally heats the entire chip of the microfluidic device and provides a uniform temperature distribution throughout the chip.

Most of the non-joule heating methods commonly used provide thermal energy to the microfluidic device do not directly provide that energy to the channels in the device. For example, many of the non-joule heating methods listed above deliver heat to an external surface of the microfluidic device, so in those methods the heat must be conducted through the body of the microfluidic device before it reaches the fluid in the channels. For example, in embodiments employing a thermal block, effecting a temperature change in the fluid contained within a microfluidic channel requires that heat be transferred to or from the block through the interface between the block and the microfluidic device, through the body of the microfluidic device, and through the interior surfaces of the channel. The need to conduct heat through the various interfaces and the body of the microfluidic device can create thermal inertia, which introduces a delay between the time the thermal block is heated or cooled and the time that heating or cooling affects the temperature within a microchannel in the device. Furthermore, since almost all non-joule heating methods to not heat the entire body of the microfluidic device uniformly, e.g. heat may be applied to only one surface of the device, or one surface of the device may be heated while another surface of the device is cooled, it is quite common to have a temperature variations within the body of the microfluidic device. In other words, the temperature in the channels of a microfluidic device may be different than the temperature on one or more of the external surfaces of the device.

Joule heating permits the precise regional control of temperature and/or heating within separate microfluidic elements of the device of the invention, e.g., within one or several separate channels, without heating other regions where such heating is, e.g., undesirable. Because the microfluidic elements are extremely small in comparison to the mass of the entire microfluidic device in which they are fabricated, such heat remains substantially localized e.g., it dissipates into and from the device before it affects other fluidic elements. In other words, the relatively massive device functions as a heat sink for the separate fluidic elements contained therein.

To selectively control the temperature of fluid or material over the length of a microchannel, the joule heating power supply of the invention can apply voltage and/or current in several optional ways. For instance, the power supply optionally applies direct current (i.e., DC), which passes through the microchannel. In order to heat the material within a microchannel, without adversely affecting the movement of a material, alternating current (i.e., AC) can be selectively applied by the power supply. The alternating current to heat the fluid can be selectively adjusted to complement any voltage or electric field applied between regions in order to move fluid in and out of the device. The microchannel(s) itself optionally, has a desired cross section (e.g., diameter width or depth) that enhances the heating effects of the current passed through it and the thermal transfer of energy from the current to the fluid.

Because electrical energy is optionally used to control temperature directly within the fluids contained in the microfluidic devices, the invention is optionally utilized in microfluidic systems that employ electrokinetic material transport systems, as noted herein. Specifically, the same electrical controllers, power supplies and electrodes can be readily used to control temperature contemporaneously with their control of material transport.

The previously described temperature control methods can be employed to carry out a melting curve analysis in a continuous flow format. In a continuous flow format, flow is continuous within a microchannel while the temperature in that channel is ramped through the range of temperatures required to generate the desired melt curve. Controlled ramping of the temperature in the channel can be accomplished using any of the joule or non-joule heating methods, possibly in conjunction with an energy sink. One benefit of a continuous flow format over a stopped flow format (i.e., the flow is stopped everywhere else in the microfluidic device) is that a continuous flow format integrates with other flow through processes (upstream or downstream) by keeping the flow moving.

In an embodiment of the present invention implementing a continuous flow format, the controlled ramping of the temperature comprises elevating the temperature of the molecule (s) by continuously increasing the temperature of the molecule(s). For example, the temperature of the molecule(s) can be continuously increased at a rate in the range of 0.1° C./second to 1° C./second. Alternatively, the temperature of the molecule(s) can be continuously increased at a slower rate such as a rate in the range of 0.01° C./second to 0.1° C./second, or at a faster rate, such as a rate in the range of 1° C./second to 10° C./second.

A melting curve analysis can be performed in continuous flow format by either varying the temperature along the length of the fluidic channel or, according to the present invention, by varying the temperature of the entire flow as it moves along the length of a microchannel, where the entire flow is uniformly heated to the same temperature. In the former case, thermal properties are measured along the length of the channel and, according to the present invention, in the latter case, thermal properties are measured at a single point as the molecular stream moves past the measurement point and as the temperature of the entire stream is increases in a uniform manner.

Controlled ramping of the temperature over the length of the microchannel can be accomplished using any of the joule or non-joule heating methods, possibly in conjunction with an energy sink. Once a steady state flow of fluid through the microchannel is established, a corresponding temperature will be established within that fluid. When Joule heating is used, a uniform temperature can be established along the length of a microchannel by fabricating the channel so that it is has a constant cross-sectional area along its length, and then applying a single electric current through that length. Almost any one of the previously described non-joule heating methods, possibly in conjunction with an energy sink, could be used to establish a uniform temperature across the length of the channel. For example, a thermal block can be placed in contact with the length of microchannel over which the uniform temperature is established, and a plurality of peltier elements can be placed at a plurality of location of the block so as to establish a uniform temperature across the block in the direction corresponding to the length direction of the microchannel When a uniform temperature is established across the length of the microchannel, in order to generate a melting curve, the temperature is uniformly varied across the entire length of the microchannel, and the physical property indicative of binding or denaturation, e.g. fluorescence, is measured at at least one point along the microchannel. In the case of fluorescence, this can be accomplished by placing at least one optical detector in optical communication with the microchannel so that the at least one optical detector samples the fluorescence at at least one point along the length of the channel. In order to generate an accurate melting curve, thermal detectors can be employed to measure the temperature along the length of the microchannel.

Figure 2A:
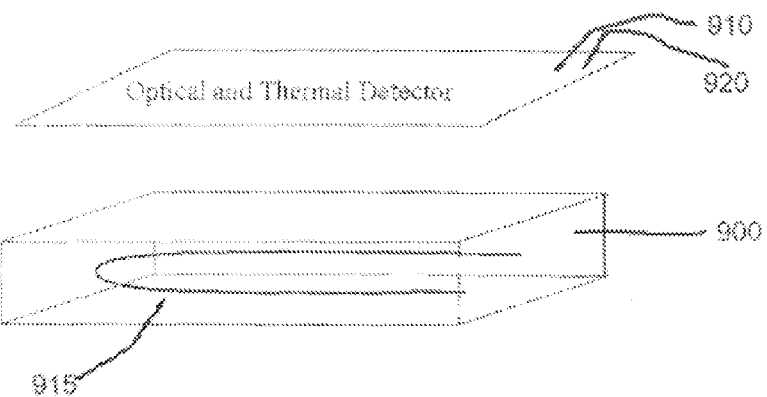
FIGS. 2A-2B are exemplary illustrations of two microfluidic systems capable of performing continuous flow format melting curve analysis according to the present invention.
Figure 2B:
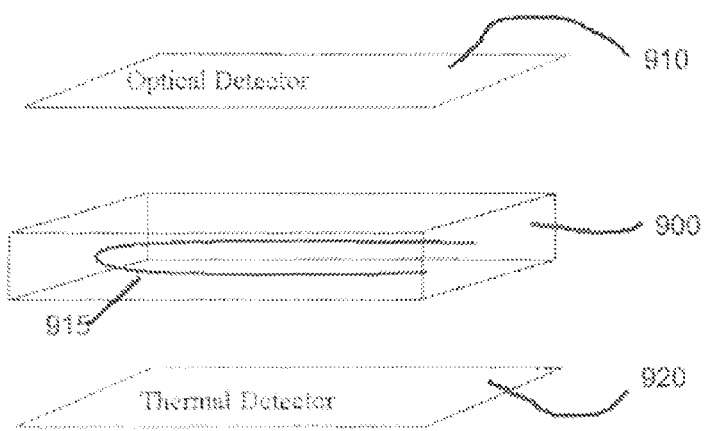

FIGS. 2A and 2B are exemplary illustrations of two microfluidic systems capable of performing a continuous flow format melting curve analysis according to the present invention. In the system shown in FIG. 2A, optical detector array 910 and thermal detector 920 are both disposed above the microfluidic device 900. In the system shown in FIG. 2B, optical detector array 910 is disposed above the microfluidic device 900, while thermal detector array 920 is disposed below the microfluidic device. In both systems, a uniform temperature is applied to the entire length of microfluidic channel 915. A fluorescence measurement is taken at at least one point along the length of microfluidic channel 915, and the combined fluorescence measurement/uniform temperature data are used as data points in the melting curve.

In the examples depicted in FIGS. 2A and 2B, the temperature of the molecule(s) being analyzed are continuously increases, or controllably ramped, as a consequence of the fluid comprising the molecule(s) flowing through the length of the microfluidic channel 915 to which the uniform temperature is applied. In embodiments where the temperature of the molecule(s) are continuously increased as a result of flow through the length of a channel to which a uniform temperature is applied, the rate at which the temperature of the molecule(s) is continuously increased can be controlled by varying one or more of the temperature being applied to the channel, the geometry of the channel (e.g., the cross-sectional area of the channel), or the flow rate of the fluid comprising the molecule(s).

Please note that the examples illustrated in FIGS. 2A and 2B are not limiting. Any microfluid system that would enable practice of the present invention is applicable. Please also note that any type of optical detector and thermal detector that would enable practice of invention is applicable. For example, thermal detectors could include, but are not limited to, thermocouples, resistance temperature detectors, thermistors, IR thermometers, or optical pyrometers. For example, optical detectors could include, but are not limited to, spectrophotometers, photodiodes, avalanche photodiodes, microscopes, scintillation counters, cameras, diode arrays, imaging systems. Photomultiplier tubes, CCD arrays, scanning detectors, galvo scanners, film, and the like, as well as a combination thereof.

Fluid Flow

The present invention utilizes a variety of methods known to persons skilled in the art for controlling the transport and direction of fluidic materials and/or materials within the devices of the present invention. These methods include, but are not limited to, pressure based flow or electrokinetic material transport. Any method for controlling the transport and direction of fluidic materials and/or materials within the devices of the present invention that would enable practice of the present invention are applicable.

Computer

As noted above, either or both of the fluid direction system and/or the detection system are coupled to an appropriately programmed processor or computer that functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an analog to digital or digital to analog converter as needed).

The computer optionally includes appropriate software for receiving user instructions, either in the form of user input into set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation.

For example, the computer is optionally used to direct a fluid direction system to control fluid flow e.g., through a variety of interconnected channels. The fluid direction system optionally directs the movement of at least a first member of a plurality, of molecules into a first member of a plurality of channels concurrent with directing the movement of at least a second member of the plurality of molecules into one or more detection channel regions. The fluid direction system also directs the movement of at least a first member of the plurality of molecules into the plurality of channels concurrent with incubating at least a second member of the plurality of molecules. It also directs movement of at least a first member of the plurality of molecules into the one or more detection channel regions concurrent with incubating at least a second member of the plurality of molecules.

By coordinating channel switching, the system directs the movement of at least one member of the plurality of molecules into the plurality of microchannels an/or one member into a detection region at a desired time interval, e.g., greater than 1 minute, about every 60 seconds or less, about every 30 seconds or less about every 10 seconds or less, about every 1.0 seconds or less, or about every 0.1 seconds or less. Each sample, with appropriate channel switching as described above, remains in the plurality of channels for a desired period of time, e.g., between about 0.1 minutes or less and about 60 minutes or more. For example the samples optionally remain in the channels for a selected incubation time of, e.g., 20 minutes.

The computer then receives the data from the one or more sensors/detectors included within the system, and interprets the data, either provides it in a user understood format, or uses that data to initiate further controller instructions, in accordance with the programming, e.g., such as in monitoring and control of flow rates, temperatures, applied voltages, and the like.

In the present invention, the computer typically includes software for the monitoring and control of materials in the channels. For example, the software directs channel switching to control and direct flow as described above. Additionally the software is optionally used to control electrokinetic or pressure-modulated injection or withdrawal of material. The injection or withdrawal is used to modulate the flow rate as described above. The computer also typically provides instructions, e.g., to the controller or fluid direction system for switching flow between channels to achieve a high throughput format.

In addition, the computer optionally includes software for deconvolution of the signal or signals from the detection system. For example, the deconvolution distinguishes between two detectably different spectral characteristics that were both detected, e.g., when a substrate and product comprise detectably different labels.

Any controller or computer optionally includes a monitor which is often a cathode ray tube ("CRT") display, a flat panel display (e.g., active matrix liquid crystal display, liquid crystal display), or the like. Data produced from the microfluidic device, e.g., thermal property curves from binding assays, is optionally displayed in electronic form on the monitor. Additionally, the data, e.g., thermal property curves, or other data, gathered from the microfluidic device can be outputted in printed form. The data, whether in printed form or electronic form (e.g., as displayed on a monitor), can be in various or multiple formats, e.g., curves, histograms, numeric series, tables, graphs and the like.

Computer circuitry is often placed in a box which includes, e.g., numerous integrated circuit chips, such as a microprocessor, memory, and interface circuits. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system.

Figure 3:
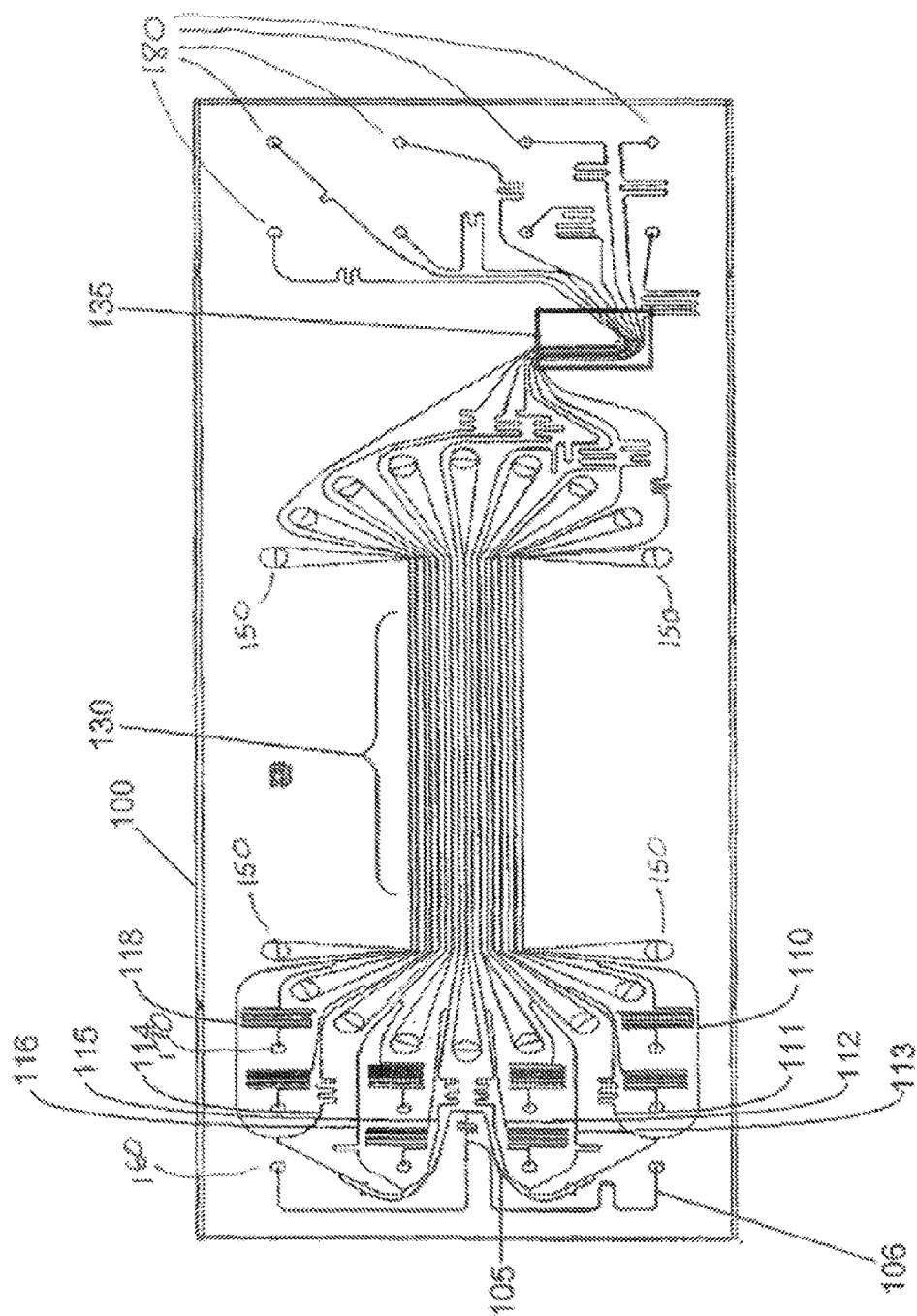
FIG. 3 depicts an example of a microfluidic device known in the art in which the present invention can be implemented.

FIG. 3 depicts an example of a microfluidic device known in the art in which the present invention can be implemented. In short, a DNA sample (e.g., a genomic DNA is brought onto chip 100 into distribution channel 105. The sample is first mixed with a common reagent from an on-chip reagent reservoir through common reagent channel 106, and then split into 8 equal aliquots into 8 independent analysis (microfluidic) channels 110-118. Each aliquot is then flowed through region 130 comprising metal traces proximal to amplification microchannels 110-118 to provide controlled heated regions of chip 100.

Melting curve analysis is performed with the length of the eight channels within detection region 135 using the continuous flow format melting curve analysis of the present invention. As previously discussed, a melting curve analysis of PCR amplification products (the amplicons) can be performed in a continuous flow process by flowing a fluid containing the amplicons through a microfluidic channel while varying the temperature of the fluid as it flows through the length of a microfluidic channel, where the fluid is uniformly heated. Accordingly, a continuous flow format melting curve analysis can be performed in the device shown in FIG. 3 by varying the temperature along the length of the eight channels traversing detection region 135, where the fluid was being uniformly heated.

Figure 4A:
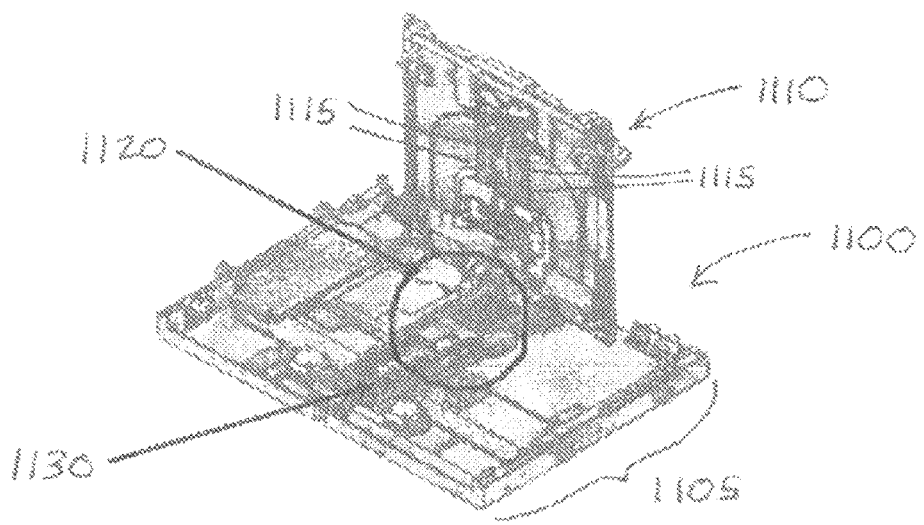
FIGS. 4A-4D depict portions of an integrated system that interfaces with the microfluidic device of FIG. 3
Figure 4B:
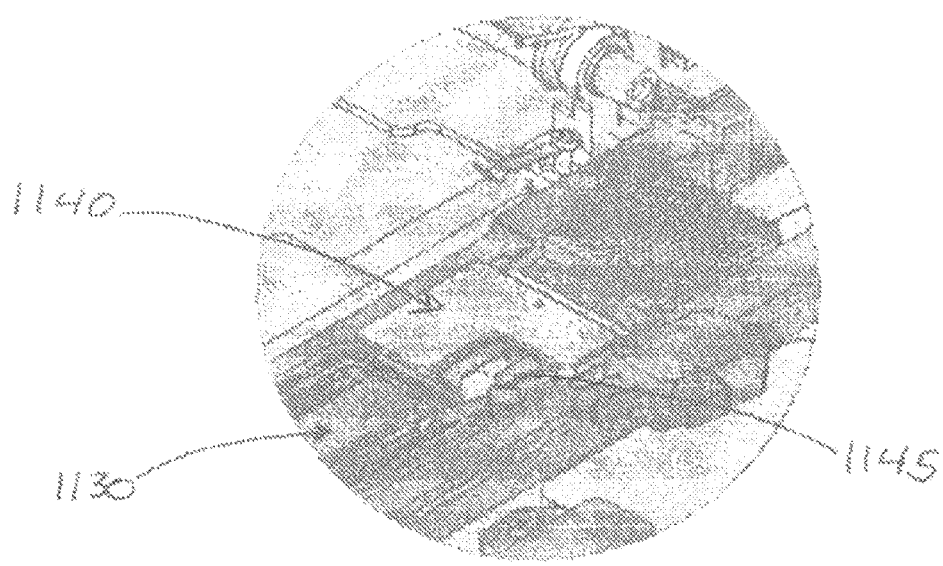
Figure 4C:
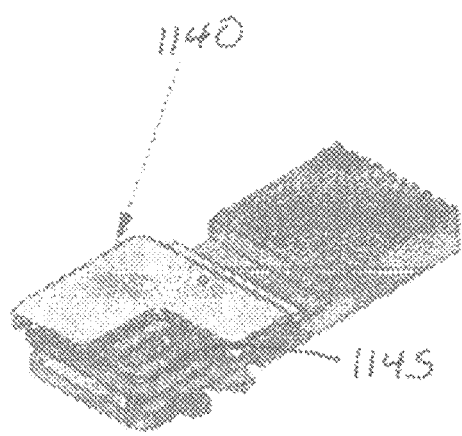
Figure 4D:
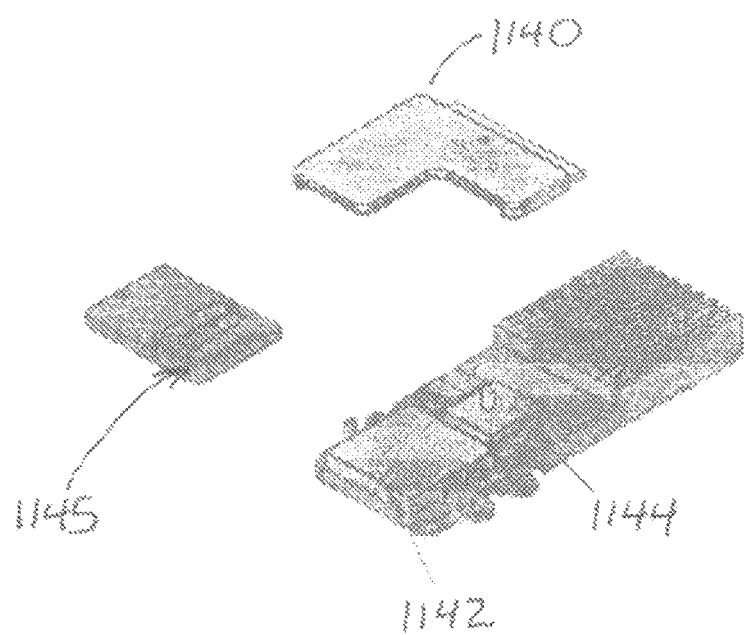

In one illustrative embodiment, a continuous flow format melting curve analysis is performed in the microfluidic device shown in FIG. 3 by placing the device into an integrated system comprising the interface module 1100 shown in FIGS. 4A-D. The interface module 1100 comprises a base portion 1105 and a clam-shell type lid 1110. The interface module 1100 is configured to receive the microfluidic device of FIG. 3 within a receiving region of the base portion 1105 that is generally within the circled area 1120 in. FIG. 4A. Once the microfluidic device is placed on top of the receiving region 1120 of the base portion, the lid 1110 is closed so that at least some of the wells (e.g., FIG. 3 160, 170, 180) at the termini of the various channels (e.g. 110-118) engage interface elements 1115 on the lid. These interface elements provide the driving forces, such as voltage or pressure, which propel fluid through the channels of the microfluidic device. Other interface elements 1115 on the lid 1110 make electrical contact with the termini 150 of the metal traces that are used as resistive heating elements to heat microfluidic channels 110-118 in the microfluidic device. The receiving region 1120 of the base plate 105 can comprise a plurality of temperature control systems that can be used to maintain a uniform temperature over the length of microfluidic channels 110-118. The temperature control systems in the embodiment of FIGS. 4A-4D are shown in increasing levels of detail in FIGS. 4B-4D.

One temperature control system comprises a fluid passage 110 that forms a sealed fluid path when a microfluidic device is placed on the receiving region 1120 and held in place by the closure of lid 1110. The interface module 1100 is configured so that the fluid passage 1130 is directly underneath region 130 of the microfluidic device. Thermal cycling required for PCR is accomplished by passing electrical current through the metal traces to heat the portion of the microfluidic channels 110-118 that pass through region 130, while the fluid contacting the backside of the microfluidic device is alternatively employed to rapidly cool that portion of the channels.

A second temperature control system is used to separately control the temperatures of the portion 135 of the microfluidic device in which a thermal melt analysis is performed, and the portion of the microfluidic device containing waste wells 180. The second temperature control system comprises a first thermal block 1140 that contacts the portion of the backside of the microfluidic device opposite the waste wells 180, and a second thermal block 1145 that contacts the portion of the backside of the microfluidic device underlying the analysis portion 135 of the microfluidic device. As can be best seen in the exploded view of FIG. 4D, the first thermal block 1140 is in thermal contact with a first thermoelectric cooling device 1144 (i.e., a peltier device), while the second thermal block 1145 is in thermal contact with a second thermoelectric cooling device 1142. The two thermoelectric cooling devices 1142, 1144 can be independently controlled, thus providing independent temperature control for the analysis portion 135 and the waste well 180 portions of the microfluidic device.

Please note that the continuous flow format melting curve analysis of the present invention is not limited to the above-described embodiment. Any system in which fluid can continuously flow through at least one microfluidic channel while varying the temperature of the entire fluid stream as it moves through the at least one microfluidic channel by uniformly heating the entire fluid stream is applicable.

Figure 5A:
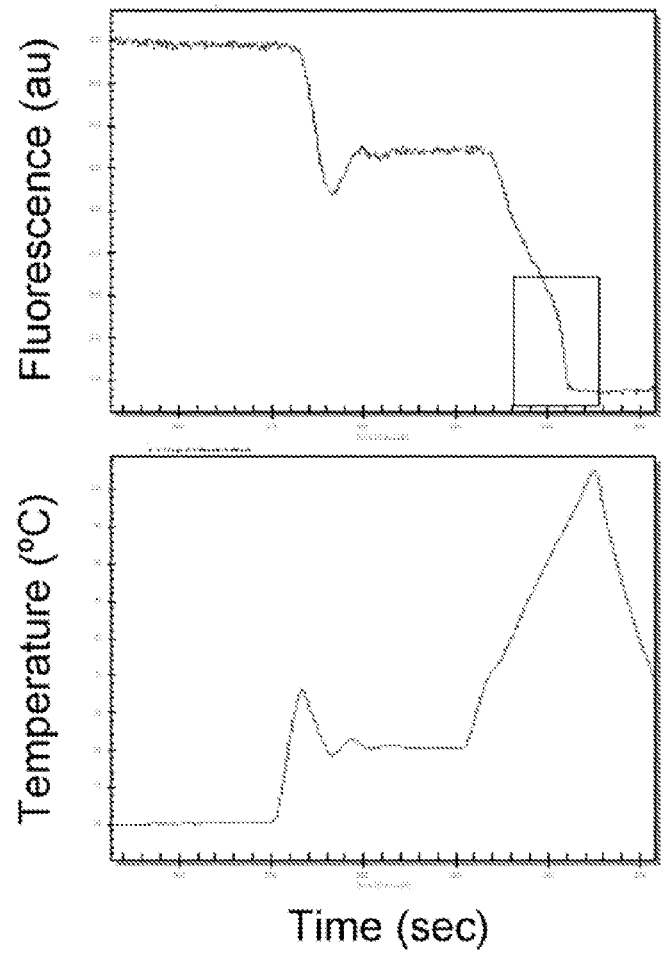
FIGS. 5A and 5B depict example data obtained using the present invention in conjunction with the microfluidic device of FIG. 3 and the integrated system of FIGS. 4A-4D.
Figure 5B:
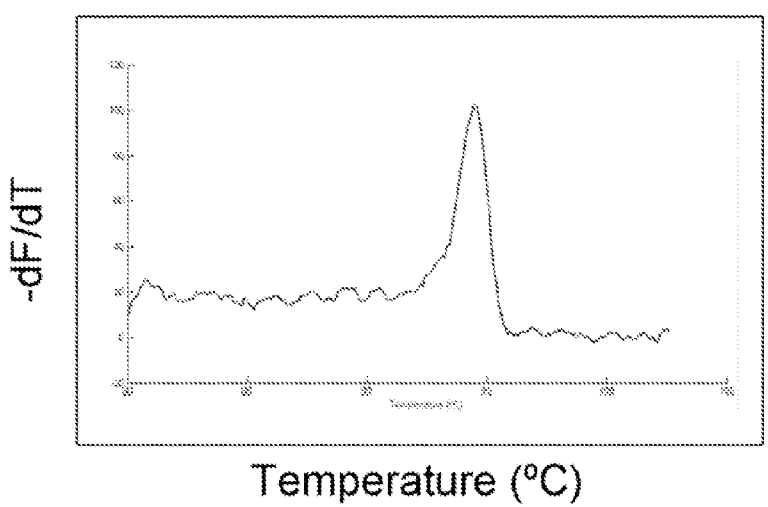

FIGS. 5A and 5B depict sample data obtained by implementing the present invention in conjunction with the microfluidic device in FIG. 3 and the instrument illustrated in FIGS. 4A-4D. As shown in FIGS. 5A and 5B, and 85 bp target is amplified from genomic DNA in the presence of the DNA binding dye SYBR Green I, which is fluorescent when bound to double-stranded DNA. In the microfluidic device, the amplification products are subjected to a thermal gradient from 60° C. to 95° C. at a rate of approximately 1° C./s and while at the same time flowing through the microfluidic channel under a pressure of ~1 psi. FIG. 5A shows the thermal ramp (below) and the change in fluorescent signal (above) over time. The boxed area in FIG. 5A is the region of the DNA thermal melt. FIG. 5B plots the negative change in fluorescence (dF) divided by the change in temperature (dT) as a function of temperature, for the boxed region in FIG. 5A. The temperature at the single peak in this plot represents the temperature at the midpoint of the DNA denaturation curve, or the $T_m$ value for the 85 bp target.

While the foregoing invention has been described in some detail for purposes of clarity and understanding, it will be clear to one skilled in the art from a reading of this disclosure that various changes in form and detail can be made without departing from the true scope the invention. For example, all the techniques and apparatus described above can be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

The invention claimed is:

1. A method of performing thermal melt analysis of a nucleic acid in a microfluidic device, the method comprising:
   (a) providing a microfluidic device having at least one microfluidic channel;
   (b) introducing fluid comprising the nucleic acid and reagents into the at least one microfluidic channel;
   (c) continuously flowing the fluid through the at least one microfluidic channel;
   (d) uniformly heating the fluid, while simultaneously continuously flowing the fluid through the at least one microfluidic channel of the microfluidic device, by applying heat at a temperature along at least a predetermined region of said microfluidic channel such that the fluid in the predetermined region has a uniform temperature, and then increasing the temperature such that the temperature of the fluid in the predetermined region is increased in a continuous and uniform manner; and
   (e) measuring, while simultaneously heating and continuously flowing the fluid through the at least one microfluidic channel of the microfluidic device, a detectable property emanating from the fluid as a function of the uniformly and continuously increased temperature, the measurements being performed at a single location along a length of the predetermined region, wherein the detectable property indicates an extent of denaturation of the nucleic acid, and wherein measuring the detectable property results in data for use in performance of the thermal melt analysis.

2. The method of claim 1, wherein the nucleic acid is DNA.

3. The method of claim 1, wherein the reagents comprise primers, a thermostable polymerase, nucleotides, and fluorescent dyes.

4. The method of claim 1, wherein the temperature of the fluid is continuously increased at a rate in the range of 0.1° C./second to 1° C./second.

5. The method of claim 1, wherein the temperature of the fluid is continuously increased at a rate in the range of 0.01° C./second to 0.1° C./second.

6. The method of claim 1, wherein the temperature of the fluid is continuously increased at a rate in the range of 1° C./second to 10° C./second.

7. The method of claim 1, wherein the temperature of the fluid is uniformly heated using joule heating.

8. The method of claim 1, wherein the temperature of the fluid is uniformly heated using non-joule heating.

9. The method of claim 8, wherein the non-joule heating comprises heating the at least one microfluidic channel using a thermal block in thermal contact with the at least one microfluidic channel.

10. The method of claim 9, wherein the thermal block maintains a uniform temperature along the length of the at least one microfluidic channel.

11. The method of claim 1, wherein the uniform temperature is generated by placing a plurality of thermal blocks in thermal contact with a plurality of peltier devices respectively, wherein the plurality of peltier devices are controlled to the same temperature.

12. The method of claim 1, wherein a uniform temperature is maintained along the length of the at least one microfluidic channel by maintaining a constant cross-section of the length of the at least one microfluidic channel and passing an electric current through the fluid flowing through the at least one microfluidic channel.

13. The method of claim 1, wherein the detectable property comprises fluorescence.

14. The method of claim 13, wherein the fluorescence is generated by FRET or a molecular beacon.

15. The method of claim 13, wherein the fluorescence is generated by a fluorescent dye, and wherein the amount of fluorescence generated by the fluorescent dye is indicative of the extent of thermal denaturation of the nucleic acid.

16. The method of claim 15, wherein the fluorescent dye is an intercalating dye.

17. The method of claim 15, wherein the fluorescent dye is ethidium bromide.

18. The method of claim 15, wherein the fluorescent dye is a minor groove binding dye.

19. The method of claim 15, wherein the fluorescent dye is a SYBR green dye.

20. The method of claim 1, wherein measuring the detectable property comprises measuring the detectable property at least one location along the length of the at at least one microfluidic channel, whereby the detectable property emanating from the fluid at a plurality of temperature is measured.

21. The method of claim 1, wherein the detectable property is fluorescence polarization.

22. The method of claim 1, wherein the detectable property is UV absorbance.

23. The method of claim 1, where in the detectable property is selected from the group consisting of heat capacity, electrical resistance, and dielectric properties.

24. A method of performing thermal melt analysis of a nucleic acid in a microfluidic device, the method comprising:
   (a) providing a microfluidic device having at least one microfluidic channel;
   (b) introducing fluid comprising the nucleic acid and reagents into the at least one microfluidic channel;
   (c) performing an amplification reaction on the nucleic acid;
   (d) continuously flowing the fluid through the at least one microfluidic channel (e) uniformly heating the fluid, while simultaneously continuously flowing the fluid through the at least one microfluidic channel of the microfluidic device, by applying heat at a temperature along at least a predetermined region of said microfluidic channel such that the fluid in the predetermined region has a uniform temperature, and then increasing the temperature such that the temperature of the fluid in the predetermined region is increased in a continuous and uniform manner; and (f) measuring, while simultaneously heating and continuously flowing the fluid through the at least one microfluidic channel of the microfluidic device, a detectable property emanating from the fluid as a function of the uniformly increased temperature, the measurements being performed at a single location along a length of the predetermined region, wherein the detectable property indicates an extent of denaturation of the nucleic acid, and wherein measuring the detectable property results in data for use in performance of the thermal melt analysis.

* * * * *